(12) United States Patent
Duerk et al.

(10) Patent No.: US 6,404,196 B1
(45) Date of Patent: Jun. 11, 2002

(54) METHOD FOR CORRECTION OF MRI MOTION ARTIFACTS AND MAIN FIELD FLUCTUATION

(75) Inventors: Jeffrey L. Duerk, Avon Lake, OH (US); Michael Wendt, Hoboken, NJ (US); Ajit Shankaranaravanan, East Cleveland, OH (US); Yiu-Cho Chung, Chicago, IL (US); Jonathan S. Lewin, Beachwood, OH (US); Elmar Merkle, Ulm (DE)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/762,026
(22) PCT Filed: Jul. 30, 1999
(86) PCT No.: PCT/US99/17288
§ 371 (c)(1),
(2), (4) Date: Apr. 4, 2001
(87) PCT Pub. No.: WO00/06245
PCT Pub. Date: Feb. 10, 2000

Related U.S. Application Data

(60) Provisional application No. 60/094,765, filed on Jul. 31, 1998.

(51) Int. Cl.[7] ................................. G01V 3/00
(52) U.S. Cl. ........................................ 324/309; 324/307
(58) Field of Search ................................. 324/307, 309, 324/312, 314, 318, 320

(56) References Cited

U.S. PATENT DOCUMENTS

| 5,243,284 A | 9/1993 | Kautz ........................ 324/309 |
| 5,534,777 A | 7/1996 | Fuderer et al. .............. 324/309 |
| 5,933,006 A | 8/1999 | Rasche et al. .............. 324/307 |
| 6,320,378 B1 * | 11/2001 | Maier et al. ................ 324/307 |

* cited by examiner

Primary Examiner—Louis Arana
(74) Attorney, Agent, or Firm—Fay, Sharpe, Fagan, Minnich & McKee, LLP (57) ABSTRACT

A method for correcting MRI motion artifacts and main field fluctuations. A series of data prints are acquired at read points along a radial axis to form a view (210). Subsequent views define a NMR data set. A processor stores the NMR data set and reconstructs an image array from a stored NMR data set by; a) reconstructing the NMR data set along a radial axis; b) producing a correction data array including correction values where each of the correction values is calculated as a function of the corresponding stored NMR datum and the stored NMR datum for the intersection of the first and subsequent projection (200) axes; c) applying the data in the correction array to the NMR data set to produce a final NMrR data set.

14 Claims, 7 Drawing Sheets

METHOD FOR CORRECTION OF MRI MOTION ARTIFACTS AND MAIN FIELD FLUCTUATION

This application claims the benefit of U.S. Provisional Application No. 60/094,765, filed Jul. 31, 1998.

BACKGROUND OF THE INVENTION

The present invention relates to magnetic resonance ("MR") imaging. It finds particular application in conjunction with correcting MRI motion artifacts and main field fluctuation and will be described with particular reference thereto. It will be appreciated, however, that the invention is also amenable to other like applications.

Magnetic resonance imaging is a diagnostic imaging modality that does not rely on ionizing radiation. Instead, it uses strong (ideally) static magnetic fields, radio-frequency ("RF") pulses of energy and magnetic field gradient waveforms. More specifically, MR imaging is a non-invasive procedure that uses nuclear magnetization and radio waves for producing internal pictures of a subject. Three-dimensional diagnostic image data is acquired for respective "slices" of an area of the subject under investigation. These slices of data typically provide structural detail having a resolution of one (1) millimeter or better.

Programmed steps for collecting data, which is used to generate the slices of the diagnostic image, are known as an MR image pulse sequence. The MR image pulse sequence includes magnetic field gradient waveforms, applied along three (3) axes, and one (1) or more RF pulses of energy. The set of gradient waveforms and RF pulses are repeated a number of times to collect sufficient data to reconstruct the slices of the image.

The data for each slice is acquired during respective excitations of the MR device. Ideally, there is little or no variations in the phase of the nuclear magnetization during the respective excitations. However, movement of the subject (caused, for example, by breathing, cardiac pulsation, blood pulsation, and/or voluntary movement) and/or fluctuations of the main magnetic field strength may change the nuclear magnetization phase from one excitation to the next. This change in the phase of the nuclear magnetization may degrade the quality of the MR data used to produce the images.

A non-phase encoded additional echo signal, prior to or after the data echo used for image generation, may be used to detect view dependent global phase variations when two-dimensional Fourier transform encoding and reconstruction algorithms are used. This "Navigator" echo passes through the center of the data space (K-space) each time, while the MR image data is ordered sequentially and linearly. Then, computational methods are used to correct the undesired view-to-view phase variation, thereby eliminating a significant source of image artifacts.

Figure 1:
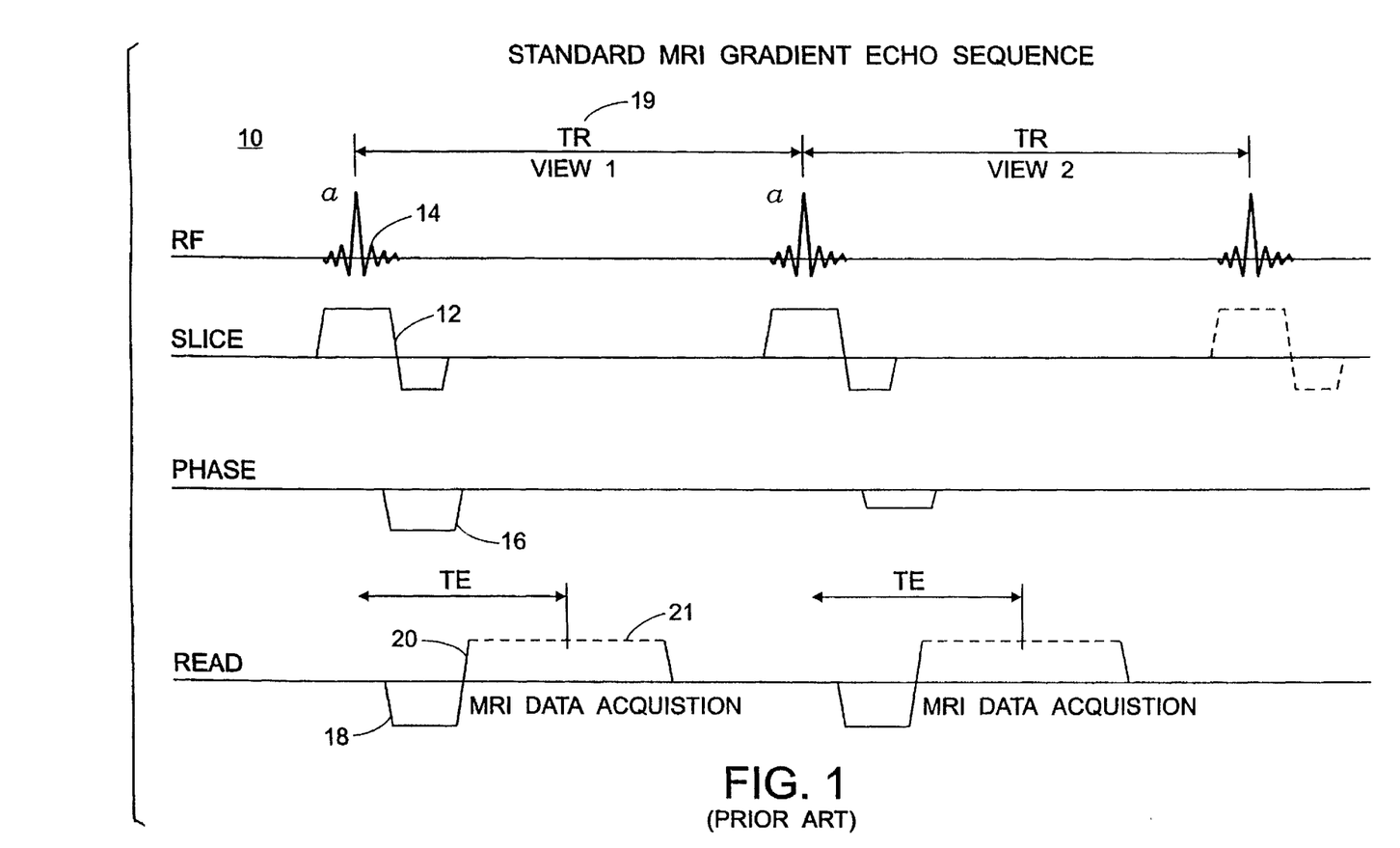
FIG. 1 is a conventional MR imaging gradient echo sequence.

With reference to FIG. 1, a typical MR imaging pulse 10 includes a slice select (frequency encoding) gradient 12 and an RF pulse 14 (i.e., the actual MR image signal). The slice select gradient 12 and the RF pulse 14 define a spatial location in which the image data occurs. A phase gradient 16 and a read gradient 18 determine how data is acquired in K-space, which is used to relate the raw data to the final image. The time interval between successive pulse cycles ("TR") is indicated as interval 19. The time interval from one pulse to the measurement of the MR signal is indicated as interval 20. The MR data is acquired during the interval 21.

The most common method for spatial encoding and reconstructing an MR image is called an N-dimensional Fourier transform ("N-DFT"). Two-dimensional Fourier transforms ("2-DFT") are used more than 90% of the time while three-dimensional Fourier transforms ("3-DFT") are used less than 10% of the time. On very rare occasions, a completely different strategy for encoding and reconstructing the data is used (e.g., wavelets, singular value decomposition, etc). Although, for the sake of simplicity, the MR imaging procedure is only described in terms of a 2-DFT comparison, it is to be understood that Fourier transforms of other dimensions are also contemplated.

In a 2-DFT MR imaging procedure, the MR image data is collected in a checkerboard fashion. Rows of the MR image data space are selected according to the phase gradient 16. The frequency encoding gradient 12 which, when combined with the actual MR image signal 14, defines the columns in the MR image data space.

Figure 2:
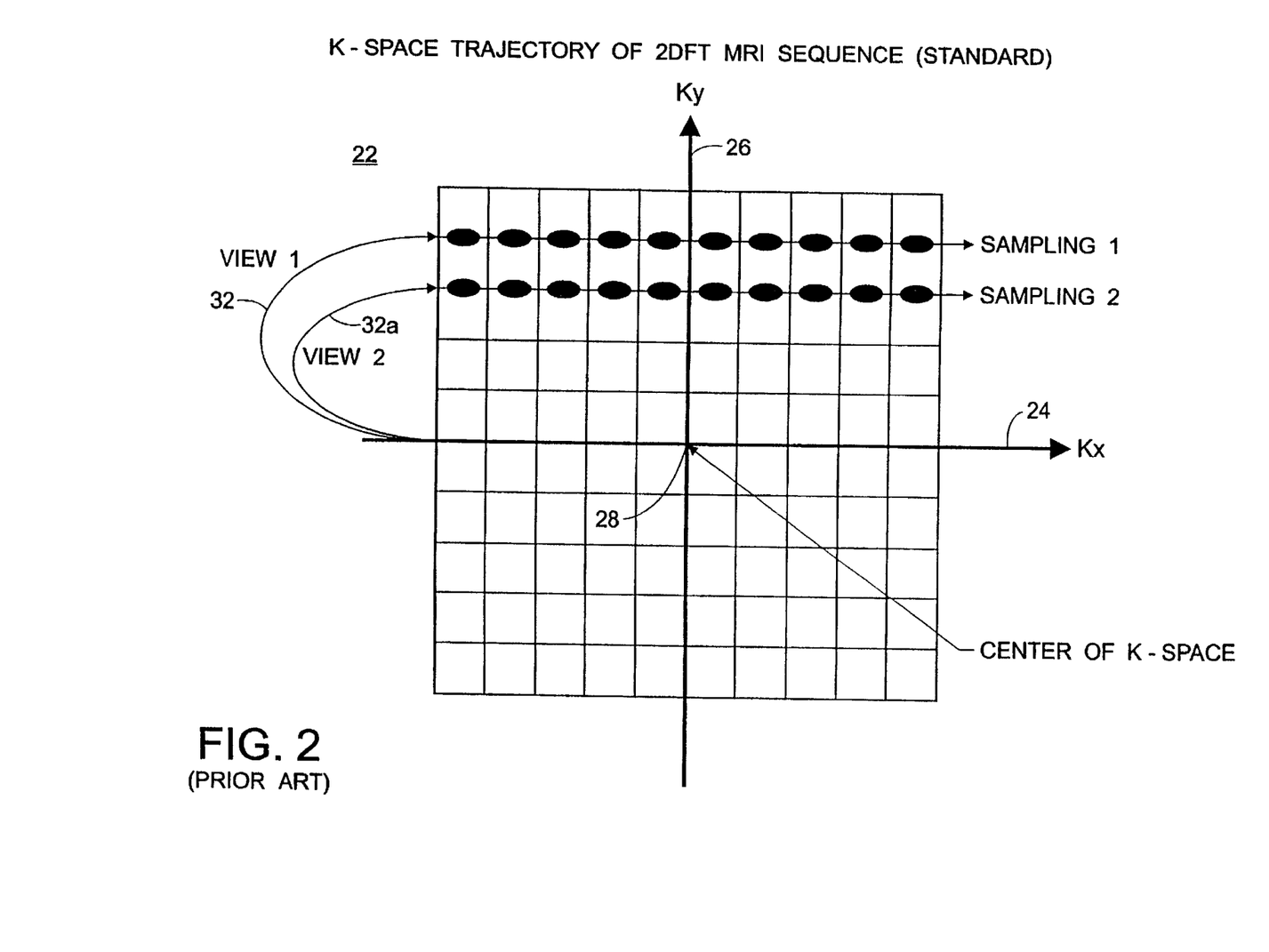
FIG. 2 is a conventional K-space trajectory of a 2-DFT MR imaging sequence.

FIG. 2 illustrates a conventional K-space 22, including a Kx axis 24 and a Ky axis 26, corresponding to the sequence 10 shown in FIG. 1. A K-space center 28, which defines an average signal amplitude in the image, is located at the intersection of the Kx and Ky axes 24, 26, respectively. A line 32 illustrates the path traversed by the typical 2-DFT MR image gradients used in the data acquisition sequence illustrated in FIG. 1. A new row 32a is collected following each repetition time ("TR") and an image is not usually reconstructed via 2-DFT until the entire data space is filled. Each point in the K-space is a complex number and, therefore, includes both real and imaginary (magnitude and phase) parts.

There are many factors that can alter the phase of the MR image signal. For example, motion through the MR image gradient waveforms and/or variations in the strength of the magnetic field during the total time of the MR image acquisition.

Because it defines an average characteristic of the object being imaged, the center of the K-space 22 is important in MR imaging. Ideally, over the course of the examination, the anatomy of the subject does not change significantly. If this were the case, no point would vary in magnitude or phase even if it is acquired multiple times. Because the center point defines the greatest amplitude in the raw data space, changes in the tissue being imaged, which may occur during TR, manifest themselves as variations in this value. Unfortunately, this point is only collected once during each normal 2-DFT acquisition. U.S. Pat. No. 4,937,526 discloses a method for forming an MR image signal prior to or after the imaging data acquisition. The trajectory in the K-space and the gradient waveforms for such an acquisition are shown in FIGS. 3 and 4.

Figure 3:
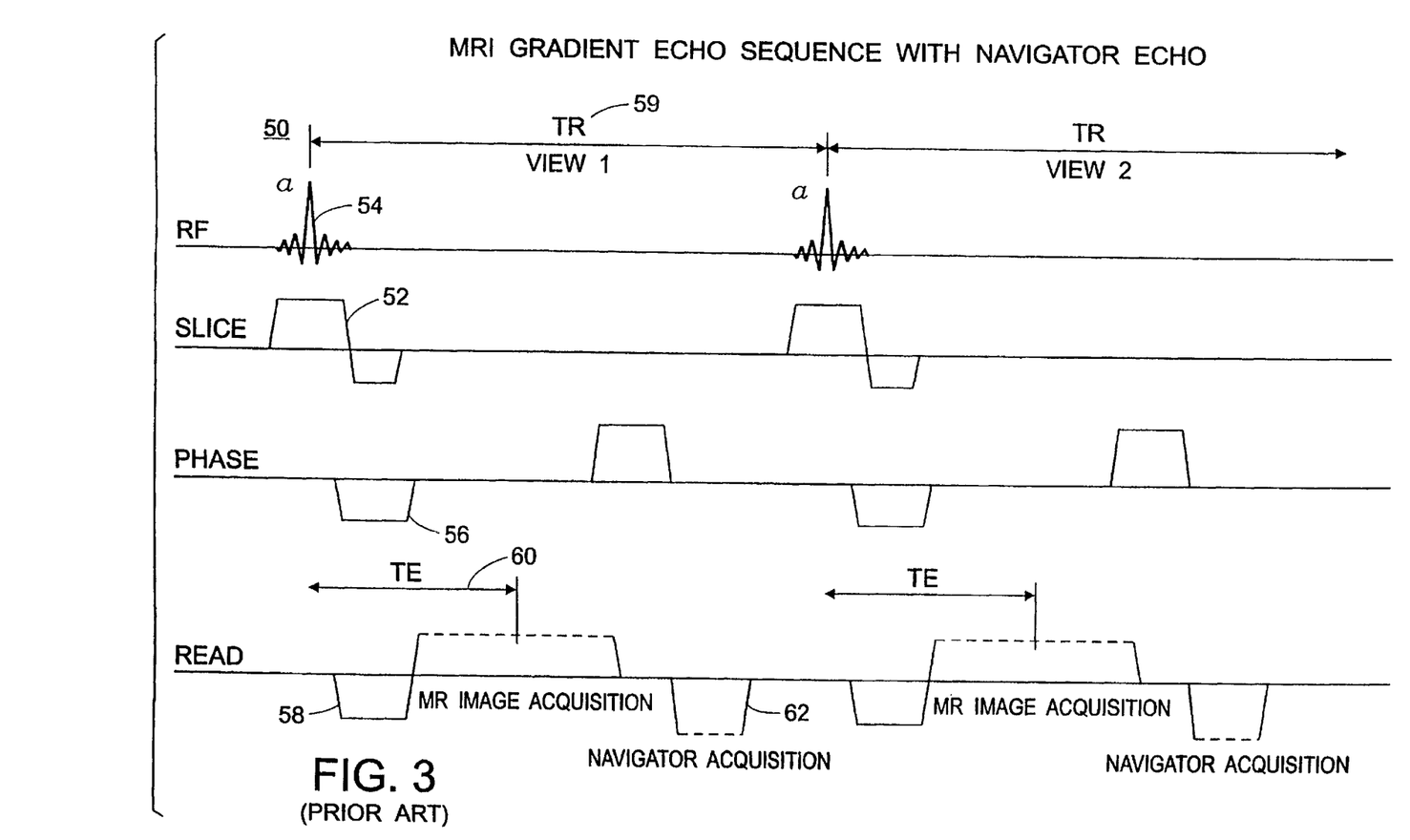
FIG. 3 is a conventional MR imaging gradient echo sequence with a Navigator echo.
Figure 4:
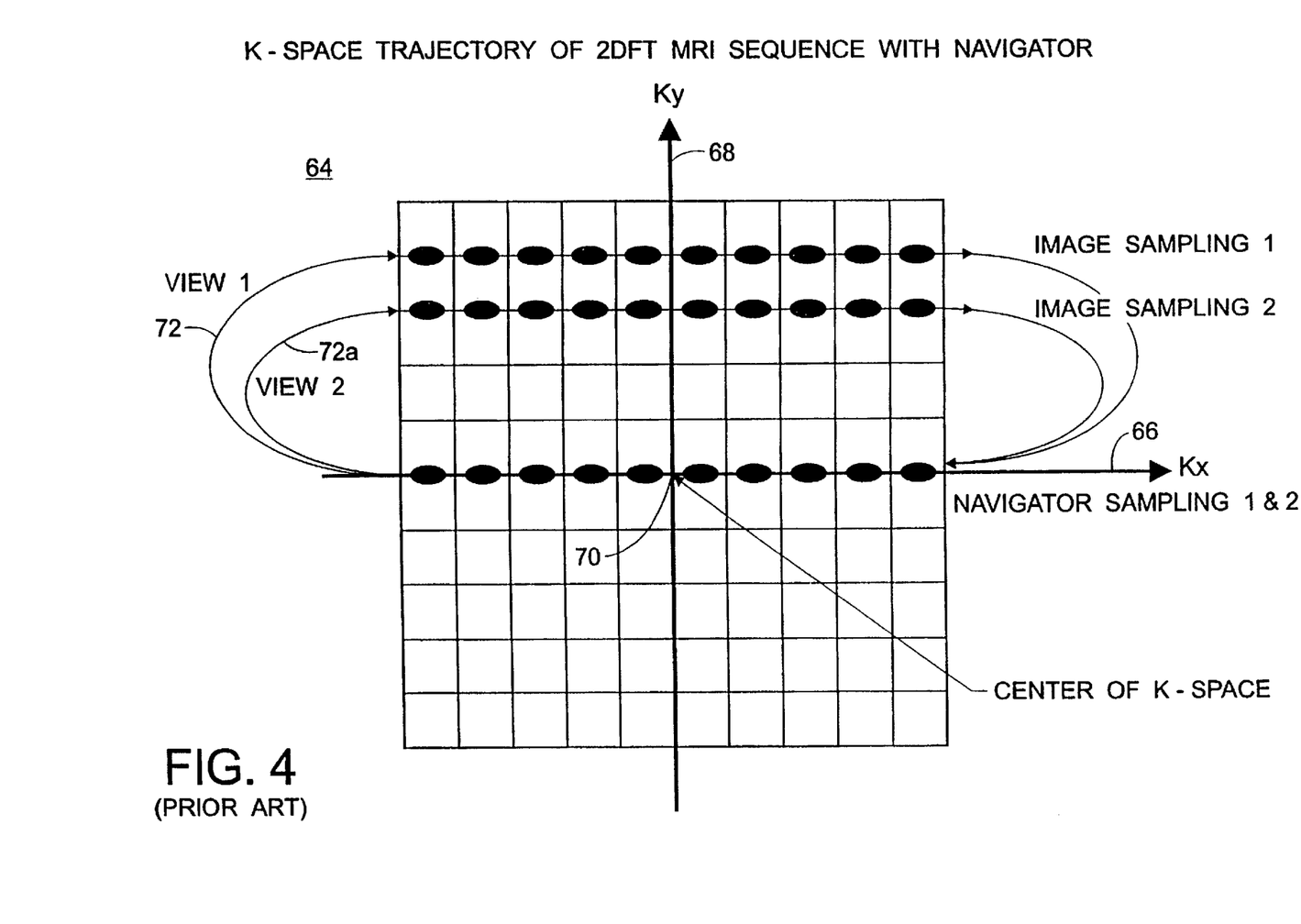
FIG. 4 is a conventional K-space trajectory of a 2-DFT MR imaging sequence with a Navigator echo.

FIG. 3 illustrates a typical MR imaging pulse with a Navigator echo 50. The pulse 50 includes a slice select (frequency encoding) gradient 52 and an RF pulse 54 (i.e., the actual MR image signal). The slice select gradient 52 and the RF pulse 54 define a spatial location in which the image data occurs. A phase gradient 56 and a read gradient 58 determine how data is acquired in K-space, which is used to relate the raw data to the final image. The time interval between successive pulse cycles ("TR") is indicated as interval 59. The time interval from one pulse to the measurement of the MR signal is indicated as interval 60.

The first portion of the TR cycle 59 shown in FIG. 3 appears to be a conventional 2-DFT acquisition. However, Navigator pulses 62 cause the supplementary trajectory to cross the center of K-space in each of the TR cycles 59.

Because the time interval between the imaging and Navigator echo is short, it is assumed that no other source of phase variation occurs beyond that imposed on the imaging data.

After the phase of each Navigator echo (i.e., the center of K-space) 62 is determined, an average is calculated across all views. The difference between the mean phase over all views and the phase of each specific view is determined and removed by appropriate well known mathematical methods. The corrected MR image data is then reconstructed to form a reduced artifact image. Again, the additional gradient waveforms are required to take the acquisition trajectory through the center of K-space so that phase information at the center of K-space can be determined for each TR. These additional gradients add time to each acquisition and reduce the temporal efficiency of the scanning while compensating for motion artifacts. This loss of efficiency is particularly detrimental to short TR rapid scanning methods routinely used in MR imaging. The loss of efficiency is often too severe to warrant their use in these common imaging methods.

FIG. 4 illustrates a K-space 64, including a Kx axis 66 and a Ky axis 68, corresponding to the sequence 50 shown in FIG. 3. A K-space center 70, which defines an average signal amplitude in the image, is located at the intersection of the Kx and Ky axes 66, 68, respectively. A line 72 illustrates the path traversed by the MR image gradients used in the data acquisition sequence illustrated in FIG. 3. A subsequent row 72a is collected following each repetition time and an image is not usually reconstructed until the entire data space is filled.

The present invention provides a new and improved apparatus and method which overcomes the above-referenced problems and others.

SUMMARY OF THE INVENTION

A magnetic resonance imaging system includes a means for generating a polarizing magnetic field within an examination region having a subject to be imaged. An excitation means generates an RF excitation magnetic field which produces transverse magnetization in nuclei subjected to the polarizing magnetic field. A receiver means senses the magnetic resonance signal produced by the transverse magnetization. A gradient means generates a magnetic field gradient to impart a read component into the magnetic resonance signal, which is indicative of a location of the transversely magnetized nuclei along a first projection axis. The gradient means generates subsequent magnetic field gradients to impart subsequent read components into the magnetic resonance signal, which are indicative of subsequent locations of the transversely magnetized nuclei along subsequent projection axes. A pulse control means is coupled to the excitation means, the gradient means, and receiver means. The pulse control means is operable to conduct a scan in which a series of data points are acquired at read points along a radial axis to form a magnetic resonance data view. Subsequent magnetic resonance data views define a magnetic resonance data set. A processor means stores the magnetic resonance data set and reconstructs an image array for a display from the stored magnetic resonance data set by:

a) reconstructing the magnetic resonance data set along the radial axis;

b) producing a correction data array including correction values (Each of the correction values is calculated as a function of the corresponding stored magnetic resonance datum and the stored magnetic resonance datum for the intersection of the first and subsequent projection axes.);

c) applying the data in the correction data array to the magnetic resonance data set to produce a final magnetic resonance data set (Effects caused by NMR phase inconsistency, including motion of the subject and temporal variations in the polarizing magnetic field, are reduced in the final magnetic resonance data set.); and d) producing the image array from the final magnetic resonance data set.

One advantage of the present invention is that effects caused by NMR phase variations in the polarizing magnetic field are reduced.

Another advantage of the present invention is that artifacts are removed without increasing the scan time.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 5:
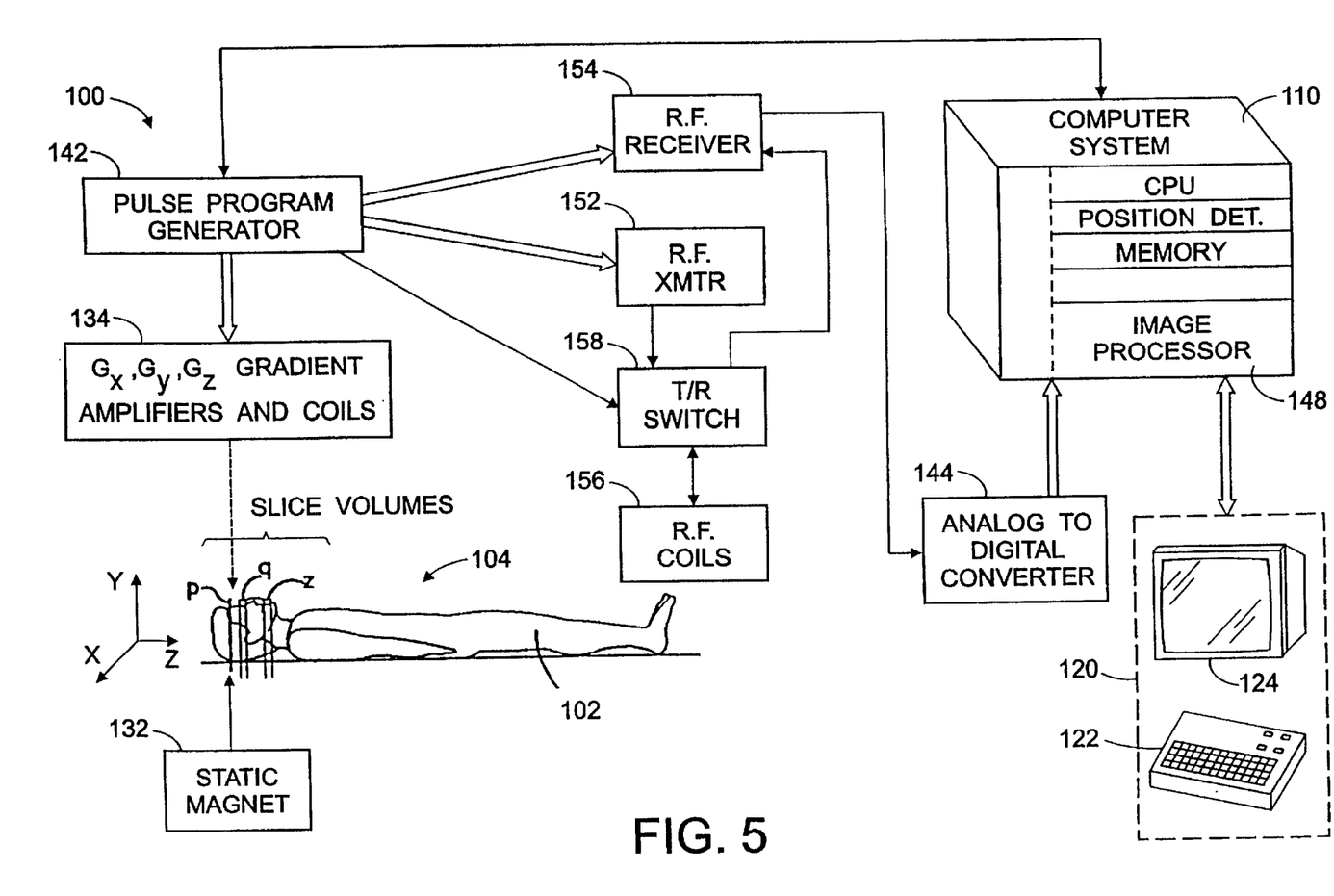
FIG. 5 illustrates, in block diagram form, an exemplary three-dimensional MR imaging system in accordance with the present invention.

FIG. 5 illustrates an exemplary MR imaging system 100 for correcting an MR image for motion artifacts and main field fluctuation in accordance with the present invention.

The operation of the MR imaging system 100 is controlled by a computer system 110. A console 120 comprising a control panel 122 and a display 124 communicates with the computer system 110 to enable an operator to control the production and display of MR images on a display 124.

To produce images with the MR image system 100, at least a portion of a subject 102 of interest is placed within an examination region 104. A static magnet 132 produces a substantially uniform, temporally constant magnetic field along a desired z-axis such that selected nuclear magnetic dipoles of the subject 102 within examination region 104 preferentially align with the magnetic field. Although illustrated as a human subject, the subject 102 may be an animal subject or any other suitable sample.

The computer system 110 communicates with a pulse program generator 142 to control a set of $G_x$, $G_y$, $G_z$ gradient amplifiers and coils 134, a radio frequency (RF) transmitter 152, and an RF receiver 154 so as to carry out a desired MR image scan sequence.

The RF transmitter 152 transmits RF pulses into the examination region 104 using RF coils 156 to cause magnetic resonance of the preferentially aligned dipoles of the subject 102 within the examination region 104. More specifically, the RF excitation magnetic field produces transverse magnetization in nuclei subjected to the polarizing magnetic field. The RF receiver 154 receives RF magnetic resonance signals detected by the RF coils 156 from the resonating dipoles of the examination region 104. The pulse program generator 142 also controls a transmit/receive (T/R) switch 158 selectively connecting the RF transmitter 152 and the RF receiver 154 to the RF coils 156. It is to be understood that in an alternate embodiment, separate transmit and receive RF coils may also be used, obviating any need for the T/R switch 158. The computer system 110 comprises an analog-to-digital converter 144 to receive the RF MR signals from the RF receiver 154 in digital form.

A processor 148 stores and processes the digitized RF MR signals to reconstruct an image representation for display on the display 124.

The gradient amplifiers and coils 134 impose time-varying magnetic field gradients with the static magnetic field along mutually orthogonal x, y, and z-axes to spatially encode the received RF MR signals. In this manner, images may be scanned along a particular one of contiguous parallel slice-volumes p, q, . . . , z defined in the examination region 104.

The computer system 110 loads software or program code defining different MR image pulse sequences into writable control storage areas of pulse program generator 142. The pulse program generator 142 executes program code corresponding to a given pulse sequence to provide suitable signals that control the operation of the RF transmitter 152, the RF receiver 154, the T/R switch 158, and the gradient amplifiers and coils 134 and thereby effectuate the given pulse sequence. The computer system 110 can specify and effectuate any suitable MR image pulse sequence for the MR image system 100 as desired.

Figure 6:
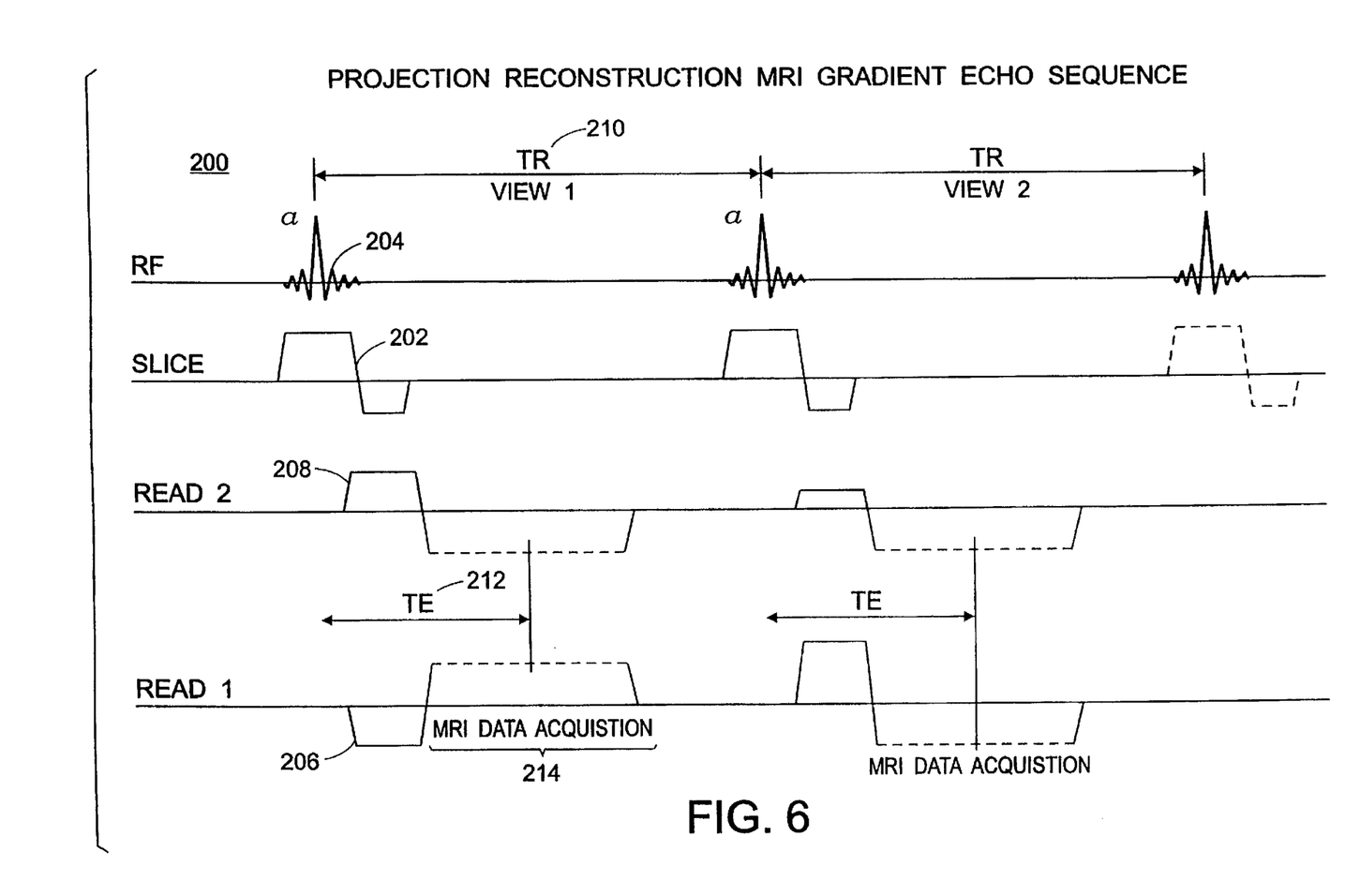
FIG. 6 illustrates a projection reconstruction MR imaging gradient echo sequence.

FIG. 6 illustrates a radial, or projection, reconstruction ("PR") 200 gradient echo sequence. The PR 200 includes a slice select gradient 202 and an RF pulse 204 (i.e., the actual MR image signal). The slice select and RF gradients 202, 204, respectively, define a spatial location in which the image data occurs.

To achieve PR data collection, a first read gradient 206 is scaled by a rotation matrix and added to a phase code axis. In this manner, there is no phase code "blip" per se. Therefore, in one sense, the PR does not include a phase encoding gradient. Instead, the PR uses the first read gradient 206 and a second read gradient 208. The first and second read gradients 206, 208, respectively, determine how data is acquired in K-space, which is used to relate the raw data to the final image. The time interval between successive pulse cycles ("TR") is indicated as interval 210. The time interval from one pulse to the measurement of the MR signal is indicated as interval 212. Data is acquired during the interval 214.

Figure 7:
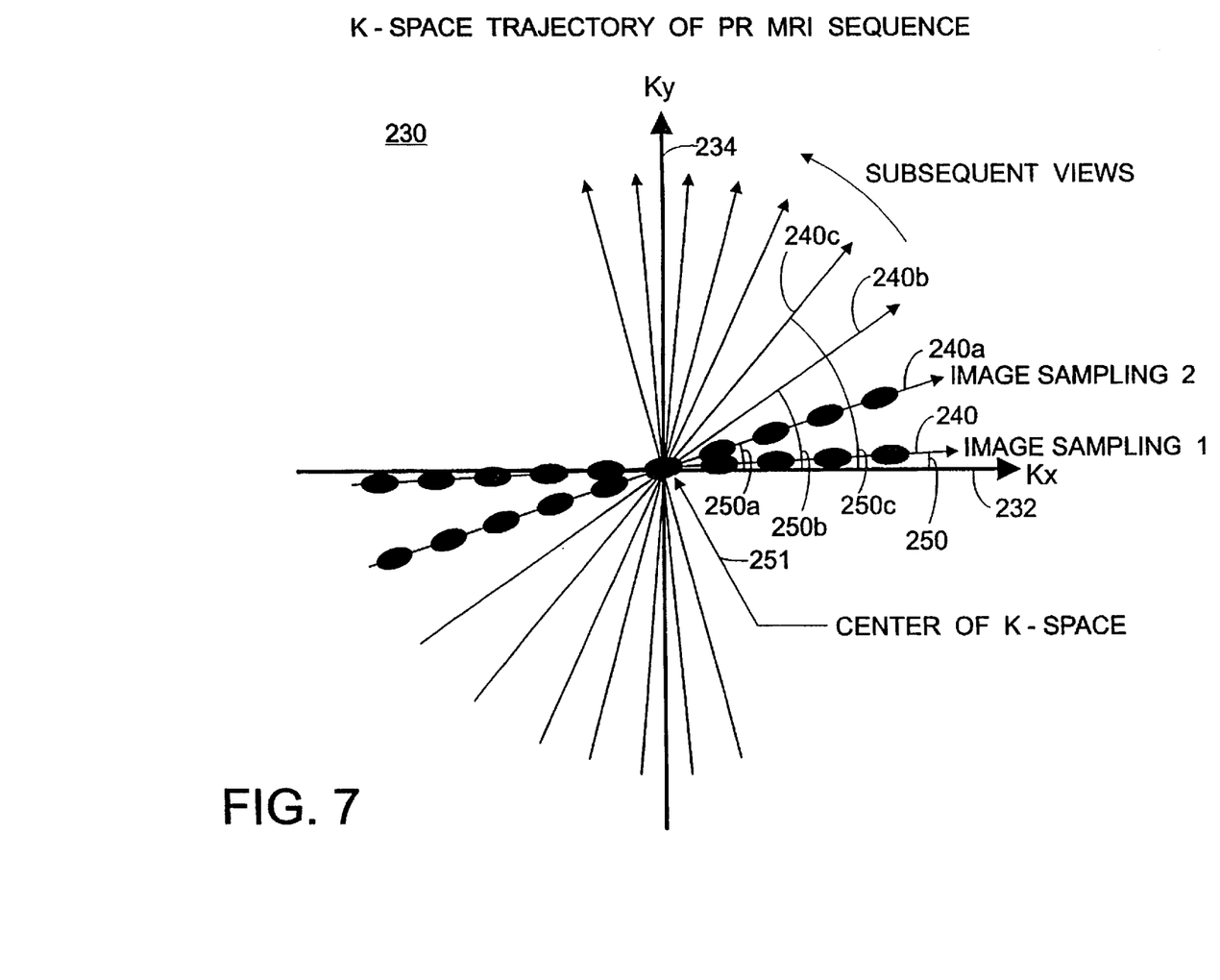
FIG. 7 illustrates a K-space trajectory of projection reconstruction for the MR imaging sequence shown in FIG. 6.

FIG. 7 illustrates K-space trajectory information 230 corresponding to the PR 200 shown in FIG. 6. First and second projection coordinate axes 232, 234, respectively, define the K-space 230.

With reference to FIGS. 5, 6, and 7, the static magnet 132 generates a polarizing magnetic field within the examination region 104 including the subject 102. The RF transmitter 152 generates the RF excitation magnetic field which produces transverse magnetization in nuclei subjected to the polarizing magnetic field. The receiver means 154 senses the magnetic resonance signal produced by the transverse magnetization.

The gradient amplifiers and coils 134 generate first and subsequent magnetic field gradients to impart respective read components into the magnetic resonance signal. The first read component is indicative of respective locations of the transversely magnetized nuclei along the first projection coordinate axis 232 (see FIG. 7).

The pulse program generator 142 conducts a scan in which a series of data points are acquired at respective read points along the radial axis 240 to form a magnetic resonance data view. It is to be understood that this process is repeated and that subsequent magnetic resonance data views for a magnetic resonance data set.

The processor 148 stores the magnetic resonance data set. Then, the processor 148 reconstructs an image array for the display 124 from the stored magnetic resonance data set by:

a) reconstructing the magnetic resonance data set along the radial axis 240;

b) producing a correction data array including correction values (Each of the correction values is calculated as a function of the corresponding stored magnetic resonance datum and the stored magnetic resonance datum for the intersection of the first and subsequent projection axes.);

c) applying the data in the correction data array to the magnetic resonance data set to produce a final magnetic resonance data set; and d) producing the image array from the final magnetic resonance data set.

Effects caused by nuclear magnetic resonance ("NMR") phase inconsistency, including motion of the subject and/or temporal variations in the polarizing magnetic field is/are reduced in the final magnetic resonance data set. In the preferred embodiment, the step of reconstructing includes projection reconstructing. However, it is to be understood that other types of reconstructing steps are also contemplated.

In the preferred embodiment an angle 250 of the radial axis 240, relative to the first projection axis 232 is determined using a scheme which causes the center of the K-space to be re-sampled during subsequent data acquisitions. For example, the angle 250 of the radial axis 240, relative to the first projection axis 232 may be determined using sine and cosine functions. However, it is to be understood that other mathematical methods are also contemplated for performing the actual phase correction.

It is to be understood that the magnetic resonance data set for the read points along the radial axis 240 corresponds to a first view. Furthermore, subsequent magnetic resonance data sets, including data at read points along respective subsequent radial axes 240a, 240b, 240c, passing through the intersection 251 of the first, second, and subsequent projection axes 232, 234, respectively, correspond to respective subsequent views. Each of the radial axes 240a, 240b, 240c in the respective subsequent views is at a respective angle 250a, 250b, 250c with respect to the first projection axis 232. The angles of the radial axes 240a, 240b, 240c relative to the first projection axis 232 are in a range spanning 180 degrees.

The frequency encoding gradients are scaled-up using the sine and cosine functions within each TR. Therefore, each acquisition traverses the center of K-space. Because each MR image acquisition passes through the center of K-space, the MR image data for each view is then used to determine the phase (due to motion or field fluctuation) as a function of view information at the center of K-space.

The apparatus and method of the present invention avoid reducing the time efficiency for removing artifacts caused by movement of the subject and/or field fluctuation when imaging the subject. The time efficiency for imaging the subject is maintained because no added gradient structures are added to the conventional PR portion of the imaging sequence.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A magnetic resonance imaging system, comprising:
   means for generating a polarizing magnetic field within an examination region including a subject to be imaged;
   excitation means for generating an RF excitation magnetic field which produces transverse magnetization in nuclei subjected to the polarizing magnetic field;
   receiver means for sensing the magnetic resonance signal produced by the transverse magnetization;
   gradient means for generating a magnetic field gradient to impart a read component into the magnetic resonance signal which is indicative of a location of the transversely magnetized nuclei along a first projection axis, the gradient means generating subsequent magnetic field gradients to impart subsequent read components into the magnetic resonance signal which are indicative of subsequent locations of the transversely magnetized nuclei along subsequent projection axes;
   pulse control means coupled to the excitation means, the gradient means, and receiver means, said pulse control means being operable to conduct a scan in which a series of data points are acquired at read points along a radial axis to form a magnetic resonance data view, subsequent magnetic resonance data views defining a magnetic resonance data set; and
   processor means for storing the magnetic resonance data set and for reconstructing an image array for a display from the stored magnetic resonance data set by:
   a) reconstructing the magnetic resonance data set along the radial axis;
   b) producing a correction data array including correction values, each of the correction values being calculated as a function of the corresponding stored magnetic resonance datum and the stored magnetic resonance datum for the intersection of the first and subsequent projection axes;
   c) applying the data in the correction data array to the magnetic resonance data set to produce a final magnetic resonance data set, effects caused by NMR phase inconsistency, including motion of the subject and temporal variations in the polarizing magnetic field being reduced in the final magnetic resonance data set; and
   d) producing the image array from the final magnetic resonance data set.

2. The magnetic resonance imaging system as set forth in claim 1, wherein the first and subsequent projection axes define a K-space.

3. The magnetic resonance imaging system as set forth in claim 1, wherein an angle of the radial axis relative to the first projection axis is determined using a scheme which causes a center of the K-space to be re-sampled during subsequent data acquisitions.

4. The magnetic resonance imaging system as set forth in claim 3, wherein the angle of the radial axis relative to the first projection axis is determined using a sine function and a cosine function.

5. The magnetic resonance imaging system as set forth in claim 1, wherein:
   the magnetic resonance data set for the read points along the radial axis corresponds to a first view; and
   subsequent magnetic resonance data sets, including data at read points along respective subsequent radial axes passing through the intersection of the first, second, and subsequent radial axes, correspond to respective subsequent views.

6. The magnetic resonance imaging system as set forth in claim 5, wherein each of the radial axes is at a respective angle with respect to the first projection axis.

7. The magnetic resonance imaging system as set forth in claim 6, wherein the angles of the radial axes relative to the first projection axis are in a range spanning at least 180 degrees.

8. A method for magnetic resonance imaging, comprising:
   generating a polarizing magnetic field, within an examination region including a subject to be imaged, using a means for generating;
   generating an RF excitation magnetic field, which produces transverse magnetization in nuclei subjected to the polarizing magnetic field, using an excitation means;
   sensing the magnetic resonance signal produced by the transverse magnetization using a receiver means;
   generating a first and subsequent magnetic field gradients, using a gradient means, to impart respective read components into the magnetic resonance signal which is indicative of a respective location of the transversely magnetized nuclei along a first projection coordinate axis;
   conducting a scan using a pulse control means, a series of data points being acquired at read points along a radial axis to form a magnetic resonance data view, subsequent views defining a magnetic resonance data set, the pulse control means being coupled to the excitation means, the gradient means, and the receiver means;
   storing the magnetic resonance data set using a processor; and
   using the processor, reconstructing an image array for a display from the stored magnetic resonance data set by:
   a) reconstructing the magnetic resonance data set along the radial axis;
   b) producing a correction data array including correction values, each of the correction values being calculated as a function of the corresponding stored magnetic resonance datum and the stored magnetic resonance datum for the intersection of the first and subsequent projection coordinate axes;
   c) applying the data in the correction data array to the magnetic resonance data set to produce a final magnetic resonance data set, effects caused by NMR phase inconsistency, including motion of the subject and temporal variations in the polarizing magnetic field, being reduced in the final magnetic resonance data set; and d) producing the image array from the final magnetic resonance data set.

9. The method for magnetic resonance imaging as set forth in claim 8, further including:

defining a K-space as a function of the first and second projection axes.

10. The method for magnetic resonance imaging as set forth in claim 9, further including:

determining an angle of the radial axis relative to the first projection axis using a scheme which causes a center of the K-space to be re-sampled during subsequent data acquisitions.

11. The method for magnetic resonance imaging as set forth in claim 10, further including:

determining an angle of the radial axis relative to the first projection axis using a sine function and a cosine function.

12. The method for magnetic resonance imaging as set forth in claim 8, further including:

defining a first view as corresponding to the magnetic resonance data set for the read points along the radial axis; and defining respective subsequent views corresponding to subsequent magnetic resonance data sets including data at read points along respective subsequent radial axes passing through the intersection of the first, second, and subsequent radial axes.

13. The method for magnetic resonance imaging as set forth in claim 12, further including:

determining an angle, with respect to the first and second projection axes, for each of the respective radial axes.

14. The method for magnetic resonance imaging as set forth in claim 13, wherein the step of defining respective subsequent views includes:

defining the respective subsequent views for radial axes having angles, relative to the first and second projection axes, in a range spanning 180 degrees.

* * * * *